(12) United States Patent  
Haramaty et al.

(10) Patent No.: US 8,734,334 B2  
(45) Date of Patent: May 27, 2014

(54) METHOD AND DEVICE FOR IMAGING AN INTERIOR SURFACE OF A CORPOREAL CAVITY

(75) Inventors: Lior Haramaty, Bergenfield, NJ (US); Ron Hadani, Cresskill, NJ (US)

(73) Assignee: NaNaMed, LLC, Northvale, NJ (US)

( * ) Notice: Subject to any disclaimer, the term of this patent is extended or adjusted under 35 U.S.C. 154(b) by 160 days.

(21) Appl. No.: 13/104,832

(22) Filed: May 10, 2011

(65) Prior Publication Data

US 2011/0295061 A1    Dec. 1, 2011

Related U.S. Application Data

(60) Provisional application No. 61/333,189, filed on May 10, 2010.

(51) Int. Cl.  
  *A61B 1/06*     (2006.01)

(52) U.S. Cl.  
  USPC .......................................... 600/170

(58) Field of Classification Search  
  CPC ........... A61B 1/00071; A61B 1/00096; A61B 1/00163; A61B 1/00174; A61B 1/00177; A61B 1/051; A61B 1/0615  
  USPC ......... 600/103, 109, 129, 160, 173, 174, 175, 600/176, 177  
  See application file for complete search history.

(56) References Cited

U.S. PATENT DOCUMENTS

| | | | |
|---|---|---|---|
| 4,398,811 A | 8/1983 | Nishioka et al. | |
| 4,699,463 A | 10/1987 | D'Amelio et al. | |
| 6,066,090 A | 5/2000 | Yoon | |
| 6,371,909 B1 | 4/2002 | Hoeg et al. | |
| 7,110,124 B2* | 9/2006 | Jensen et al. | 356/626 |
| 7,553,276 B2* | 6/2009 | Iddan | 600/160 |
| 7,621,869 B2 | 11/2009 | Ratnakar | |
| 2002/0052547 A1* | 5/2002 | Toida | 600/425 |
| 2003/0191369 A1* | 10/2003 | Arai et al. | 600/173 |
| 2004/0220478 A1* | 11/2004 | Wallace et al. | 600/476 |
| 2004/0254424 A1* | 12/2004 | Simkulet et al. | 600/176 |
| 2005/0049462 A1* | 3/2005 | Kanazawa | 600/170 |
| 2005/0090709 A1 | 4/2005 | Okada et al. | |
| 2006/0217593 A1* | 9/2006 | Gilad et al. | 600/160 |
| 2007/0015989 A1 | 1/2007 | Desai et al. | |
| 2007/0167682 A1 | 7/2007 | Goldfarb et al. | |
| 2007/0177008 A1 | 8/2007 | Bayer et al. | |
| 2007/0177009 A1 | 8/2007 | Bayer et al. | |
| 2007/0185384 A1 | 8/2007 | Bayer et al. | |
| 2007/0244354 A1 | 10/2007 | Bayer | |
| 2007/0270642 A1 | 11/2007 | Bayer et al. | |
| 2007/0279486 A1 | 12/2007 | Bayer et al. | |
| 2007/0293720 A1 | 12/2007 | Bayer | |

(Continued)

FOREIGN PATENT DOCUMENTS

WO     2009002467     12/2008

*Primary Examiner* — Philip R Smith  
(74) *Attorney, Agent, or Firm* — William H. Dippert; Eckert Seamans Cherin & Mellott, LLC

(57) ABSTRACT

An endoscopic imaging catheter is configured for insertion, optionally via a longitudinal channel of an endoscopic insertion tube. The endoscopic imaging catheter includes reflecting and optical elements and an imaging element. The reflecting element reflects onto the imaging element through the optical element side and rear views of at least a portion, or the entire 360° view of a wall encircling an intrabody lumen around the axis of said the longitudinal channel.

13 Claims, 4 Drawing Sheets

(56) References Cited

U.S. PATENT DOCUMENTS

| | | |
|---|---|---|
| 2008/0021274 A1 | 1/2008 | Bayer et al. |
| 2008/0071288 A1 | 3/2008 | Larkin et al. |
| 2008/0130108 A1 | 6/2008 | Bayer et al. |
| 2008/0253686 A1 | 10/2008 | Bayer |
| 2009/0012357 A1 | 1/2009 | Suzushima et al. |
| 2009/0213211 A1 | 8/2009 | Bayer et al. |
| 2009/0231419 A1 | 9/2009 | Bayer |
| 2009/0306474 A1* | 12/2009 | Wilson .......................... 600/109 |
| 2010/0016662 A1* | 1/2010 | Salsman et al. ............... 600/109 |
| 2010/0081873 A1* | 4/2010 | Tanimura et al. ............. 600/109 |

* cited by examiner

METHOD AND DEVICE FOR IMAGING AN INTERIOR SURFACE OF A CORPOREAL CAVITY

CROSS-REFERENCE TO RELATED APPLICATION

This application is based upon and claims the benefit of the filing date of commonly assigned U.S. Provisional Patent Application Ser. No. 61/333,189, filed May 10, 2010, incorporated herein by reference.

FIELD OF THE INVENTION

The present invention relates to an endoscope assembly. More particularly, the invention relates to an auxiliary endoscopic imaging catheter and a method of performing a medical procedure.

BACKGROUND OF THE INVENTION

An endoscope is a medical or industrial device comprising a flexible or rigid tube and a camera or fiber optics mounted on the distal end of the tube. The endoscope is insertable into an internal body cavity through a body orifice or a surgical incision to examine the body cavity and tissues as part of a diagnosis or therapeutic procedure. The tube of the endoscope has one or more longitudinal channels, which may be used for irrigation, or suction, or through which an instrument can reach the body cavity to take samples of suspicious tissues or to perform other surgical procedures such as polypectomy, tissue ablation or localized drag delivery.

There are many types of endoscopes, and they are named in relation to the organs or areas with which they are used. For example, gastroscopes are used for examination and treatment of the esophagus, stomach, and duodenum; colonoscopes are used for examination and treatment of the colon; bronchoscopes are used for examination and treatment of the lungs and bronchi; laparoscopes are used for examination and treatment of the peritoneal cavity; sigmoidoscopes are used for examination and treatment of the rectum and the sigmoid colon; arthroscopes are used for examination and treatment of joints; cystoscopes are used for examination and treatment of the urinary bladder; ureteroscopes are used for examination and treatment of the ureters and kidneys; and angioscopes are used for examination and treatment of blood vessels.

Many conventional endoscopes include a single forward-viewing fiber bundle or a camera mounted at the distal end of the endoscope that captures and transmits an image to an eyepiece, in the case of fiber bundle, or to a video display monitor at the proximal end. The image is used to assist a medical professional in advancing the endoscope into a body cavity and looking for abnormalities. The camera provides the medical professional with a two-dimensional view from the distal end of the endoscope. To capture an image from a different angle or in a different portion of the endoscope, the endoscope must be maneuvered, repositioned, articulated, or moved back and forth. All these maneuvers of the endoscope prolong the procedure and cause added discomfort, complications, and risks to the patient. Additionally, in an environment such as the lower gastro-intestinal tract, flexures, tissue folds, and unusual geometries of the organ may prevent the endoscope's forward-looking camera from viewing behind tissue folds, flexures, and other "hidden" areas of the lumen. The inability to view behind the folds, flexures, and other "hidden" areas may cause a potential polyp to be missed during colonoscopy.

OBJECTS OF THE INVENTION

It is an object of the invention to overcome the problem of limited forward-looking characteristics of known endoscopes.

It is also an object of the invention to provide an endoscopic imaging catheter comprising:
a longitudinally extending shaft having a proximal end, a distal end, and an outer surface, wherein the distal end comprises a portion that is transparent;
a source of light in the distal end of the shaft;
a proximally facing reflective element positioned within the distal end of the shaft; and
an imaging element positioned within the distal end of the shaft and in communication with the reflective element,
wherein the imaging element in the distal end of the shaft can obtain images of up to 360°, preferably 360°, around the distal end of the shaft and in a proximal or substantially proximal direction.

It is a further object of the invention to provide an auxiliary endoscopic imaging catheter for insertion via a longitudinal working channel in an endoscope or an endoscopic insertion tube, comprising:
a longitudinally extending shaft having a proximal end, a distal end, and an outer surface, wherein the distal end comprises a portion that is transparent;
a source of light in the distal end of the shaft;
a proximally facing reflective element positioned within the distal end of the shaft; and
an imaging element positioned within the distal end of the shaft and in communication with the reflective element,
wherein the imaging element in the distal end of the shaft can obtain images of up to 360°, preferably 360°, around the distal end of the shaft and in a proximal or substantially proximal direction.

These and other objects of the invention will become more apparent from the discussion below.

SUMMARY OF THE INVENTION

In one embodiment, the present invention provides for a retrograde or rear view that augments the forward-looking view of a conventional endoscope. This embodiment provides for a rear-looking video camera and a light source, mounted on the distal end of an endoscopic insertion tube, that together provide for an auxiliary endoscopic imaging catheter.

Optionally, the auxiliary endoscopic imaging catheter is designed to be insinuated into a channel of a conventional endoscope and to exit from the distal opening of the channel of the conventional endoscope.

According to an embodiment of the invention, the endoscope is an auxiliary endoscopic imaging catheter. The endoscope assembly includes a main endoscope that includes an insertion tube, a forward-viewing imaging device mounted at a distal end area of the insertion tube, and a channel extending through the insertion tube. The auxiliary endoscopic imaging catheter extends through the channel of the insertion tube of the main endoscope and exits from a distal opening of the channel of the insertion tube.

According to another embodiment of the invention, the auxiliary endoscopic imaging catheter is moveable along the channel of the main endoscope to adjust the distance between the camera and light source of the auxiliary endoscopic catheter and the camera and light source of the main endoscope in order to avoid optical interaction or cross-talk between them.

In an exemplary embodiment of the invention, the camera of the auxiliary endoscopic imaging catheter allows for capturing at least a portion of a fold, flexure, or other area "hidden" to a forward-looking main endoscope, without maneuvering or articulating the tip of the main endoscope.

Optionally, parts or the entire auxiliary endoscopic imaging catheter are disposable and/or replaceable.

Optionally, the auxiliary endoscopic imaging catheter is flexible and does or does not include a steering or articulation mechanism.

In accordance with another embodiment of the invention, an auxiliary endoscopic imaging catheter for insertion via a longitudinal channel of a main endoscope's insertion tube, comprises a distal head which includes a rear view camera and light source. The rear view camera includes optical components including a mirror, which without any movement, continuously reflects to the camera the surface of the cavity located behind to the side and optionally in front of the camera.

The present invention, in certain embodiments thereof, relates to a method and an apparatus for intrabody imaging and, more particularly, but not exclusively, to a method and an endoscope for imaging to the side of the endoscope.

According to certain embodiments of the present invention, there is provided an endoscopic imaging catheter which is optionally designed to be inserted via a working channel of an endoscopic insertion tube, and which allows the imaging of walls which encircle an intrabody lumen. Optionally, this catheter is used for imaging portions of the wall which are outside the view of a camera provided with the endoscope insertion tube, for example, portions of which are behind the view of such camera.

Optionally, both an insertion tube imager and a catheter imager are used together to image different and possibly overlapping parts of the intrabody lumen, optionally simultaneously. Optionally or alternatively, illumination is shared between the two imaging systems. Optionally, the imaging catheter includes an illumination guide or means. Optionally, such illumination means is arranged so that it does not directly illuminate the imaging system of the imaging catheter. Optionally or alternatively, the imaging catheter imaging system is arranged so that it is not directly illuminated by an illumination means of the endoscope, for example, if the catheter is advanced a sufficient amount. Optionally, this direct illumination is prevented by recessing one or more parts of the imaging system of the imaging catheter so that the body of the imaging catheter blocks light from the illumination means of the endoscope. Optionally or alternatively to changing an imaging axis of an imaging element of the imaging catheter, the illumination is reflected, for example, using a mirror, towards the wall of the intrabody lumen, optionally to overlap with a visual field of the endoscopic imaging catheter.

In another embodiment of the invention, the endoscopic imaging catheter is covered with a protective sheath, optionally disposable. Such a sheath, which is optionally made from a relatively inexpensive, transparent material such as polyethylene terephthalate (PET) or polycarbonate, allows using the endoscopic imaging catheter in multiple procedures, with multiple patients, without having to perform time consuming disinfective reprocessing procedures. Such a sheath may reduce the price of each one of the procedures. Optionally, such a sheath is designed for a single use to reduce the risk of patient to patient cross contamination. For example, the sheath may tear when removed or may be elastic and provided in everted form or rolled-up for mounting on the imaging catheter.

In another embodiment of the invention, the endoscopic imaging catheter is sized and shaped so that it can be used with a plurality of different endoscope insertion tube designs.

In another embodiment of the invention, the imaging catheter includes an imaging element and an optional image axis changing element (e.g., a mirror). Optionally, these elements are aligned along the longitudinal axis of the shaft.

Optionally, the imaging element and/or mirror are arranged to simultaneously image on multiple sides of or around the imaging catheter.

In another embodiment of an auxiliary endoscopic imaging catheter of the invention, for insertion via a working or longitudinal channel of an endoscopic insertion tube, the catheter comprises:

an optical element and an imaging element, wherein the optical element and the imaging element are capable of capturing an image of up to 360° of the side and rearward-looking views of a corporeal wall encircling an intrabody lumen.

In another embodiment of an auxiliary endoscopic imaging catheter of the invention, the optical element comprises a reflecting optical element that is distal or proximal in relation to said imaging element when the catheter exits the longitudinal channel.

In another embodiment of an auxiliary endoscopic imaging catheter of the invention, the optical element is distal or proximal in relation to said imaging element when the catheter exits the longitudinal channel.

In another embodiment of an auxiliary endoscopic imaging catheter of the invention, the catheter further comprises an illumination source located proximal or distal to the imaging element.

In another embodiment of an auxiliary endoscopic imaging catheter of the invention, the illumination source is structured and mounted as a 360° ring thus illuminating the side, rear, and optionally front field of view of said imaging element, approximately 360° around the longitudinal axis of the auxiliary endoscopic imaging catheter.

In another embodiment of an auxiliary endoscopic imaging catheter of the invention, an illumination source is located proximal or distal to the optical element.

In another embodiment of an auxiliary endoscopic imaging catheter of the invention, the illumination source is structured and mounted as a 360° ring thus illuminating the side, rear, and optionally front field of view of said imaging element, approximately 360° around the longitudinal axis of the auxiliary endoscopic imaging catheter.

In another embodiment of an auxiliary endoscopic imaging catheter of the invention, an illumination source is attached to one end of a rotatable wire.

In another embodiment of an auxiliary endoscopic imaging catheter of the invention, rotating or wobbling of said rotatable wire in its other end around its long axis allows rotating or wobbling said illumination source to cover a motion of 360° around the longitudinal axis of the auxiliary endoscopic imaging catheter, allowing the illumination of said side and rear view or at least a portion, of the entire 360° view of a wall encircling an intrabody lumen, which is located behind the imaging element, around the axis of said the longitudinal channel.

In another embodiment of an auxiliary endoscopic imaging catheter of the invention, an illumination source comprises a single light source or a plurality of light sources.

In another embodiment of an auxiliary endoscopic imaging catheter of the invention, the illumination source comprises one or more LEDs.

In another embodiment of an auxiliary endoscopic imaging catheter of the invention, said endoscopic insertion tube is capable of performing a procedure selected from the group consisting of anoscopy, arthroscopy, bronchoscopy, colonoscopy, cystoscopy, esophagogastro-duodenoscopy (EGD), laparoscopy, and sigmoidoscopy.

In another embodiment of an auxiliary endoscopic imaging catheter of the invention, a system comprises an endoscopic imaging catheter and a sheath sized and shaped to cover said the auxiliary endoscopic imaging catheter.

In an embodiment of a method of the invention of probing an intrabody lumen, the method comprises:

inserting a standard endoscope having a working channel into a patient's organ or corporeal lumen;

inserting an endoscopic imaging catheter of claim 1 into the working channel; and advancing the distal tip of the imaging catheter distal to the working channel of the endoscope, wherein first and second images of the intrabody lumen and a segment of an inner wall encircling said intrabody lumen can be captured.

In one embodiment of the invention, first and second images are captured substantially simultaneously.

In an embodiment of an endoscopic imaging catheter of the invention for capturing rearward images, the catheter comprises:

an optical element;
an imaging element; and
an illumination source, wherein the optical element and the imaging element are capable of capturing an image of up to 360° of the side and rearward-looking views of a corporeal wall encircling an intrabody lumen and wherein the illumination source comprises a 360° ring capable of illuminating up to 360° around a longitudinal axis of the catheter.

In an embodiment of an endoscopic imaging catheter of the invention for capturing rearward images, the optical element comprises a reflecting optical element that is distal in relation to said imaging element when the catheter exits the longitudinal channel.

In an embodiment of an endoscopic imaging catheter of the invention for capturing rearward images, the optical element is distal in relation to said imaging element when the catheter exits the longitudinal channel.

In an embodiment of an endoscopic imaging catheter of the invention for capturing rearward images, the illumination source is located proximal to the imaging element.

In an embodiment of an endoscopic imaging catheter of the invention for capturing rearward images, the illumination source is structured and mounted as a 360° ring thus illuminating the side, rear, and optionally front field of view of said imaging element, up to 360° around the longitudinal axis of the auxiliary endoscopic imaging catheter.

In an embodiment of an endoscopic imaging catheter of the invention for capturing rearward images, the illumination source is located proximal to the optical element.

In an embodiment of an endoscopic imaging catheter of the invention for capturing rearward images, the illumination source is structured and mounted as a 360° ring thus illuminating the side, rear, and optionally front field of view of said imaging element, up to 360° around the longitudinal axis of the auxiliary endoscopic imaging catheter.

In an embodiment of an endoscopic imaging catheter of the invention for capturing rearward images, the illumination source is attached to one end of a rotatable wire.

In an embodiment of an endoscopic imaging catheter of the invention for capturing rearward images, rotating or wobbling of said rotatable wire in its other end around its longitudinal axis allows rotating or wobbling said illumination source to cover a motion of 360° degrees around the longitudinal axis of the auxiliary endoscopic imaging catheter, allowing the illumination of said side and rear view or at least a portion, of the entire 360° view of a wall encircling an intrabody lumen, which is located behind the imaging element, around the axis of said the longitudinal channel.

In an embodiment of an endoscopic imaging catheter of the invention for capturing rearward images, the illumination source comprises a single light source or a plurality of light sources.

In an embodiment of an endoscopic imaging catheter of the invention for capturing rearward images, the illumination source comprises one or more LEDs.

In an embodiment of an endoscopic imaging catheter of the invention for capturing rearward images, the endoscopic imaging catheter is capable of performing a procedure selected from the group consisting of anoscopy, arthroscopy, bronchoscopy, colonoscopy, cystoscopy, esophagogastro-duodenoscopy (EGD), laparoscopy, and sigmoidoscopy.

In an embodiment of an endoscopic imaging catheter of the invention for capturing rearward images, a system comprises an endoscopic imaging catheter and a sheath sized and shaped to cover said endoscopic imaging catheter.

DETAILED DESCRIPTION OF THE INVENTION

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
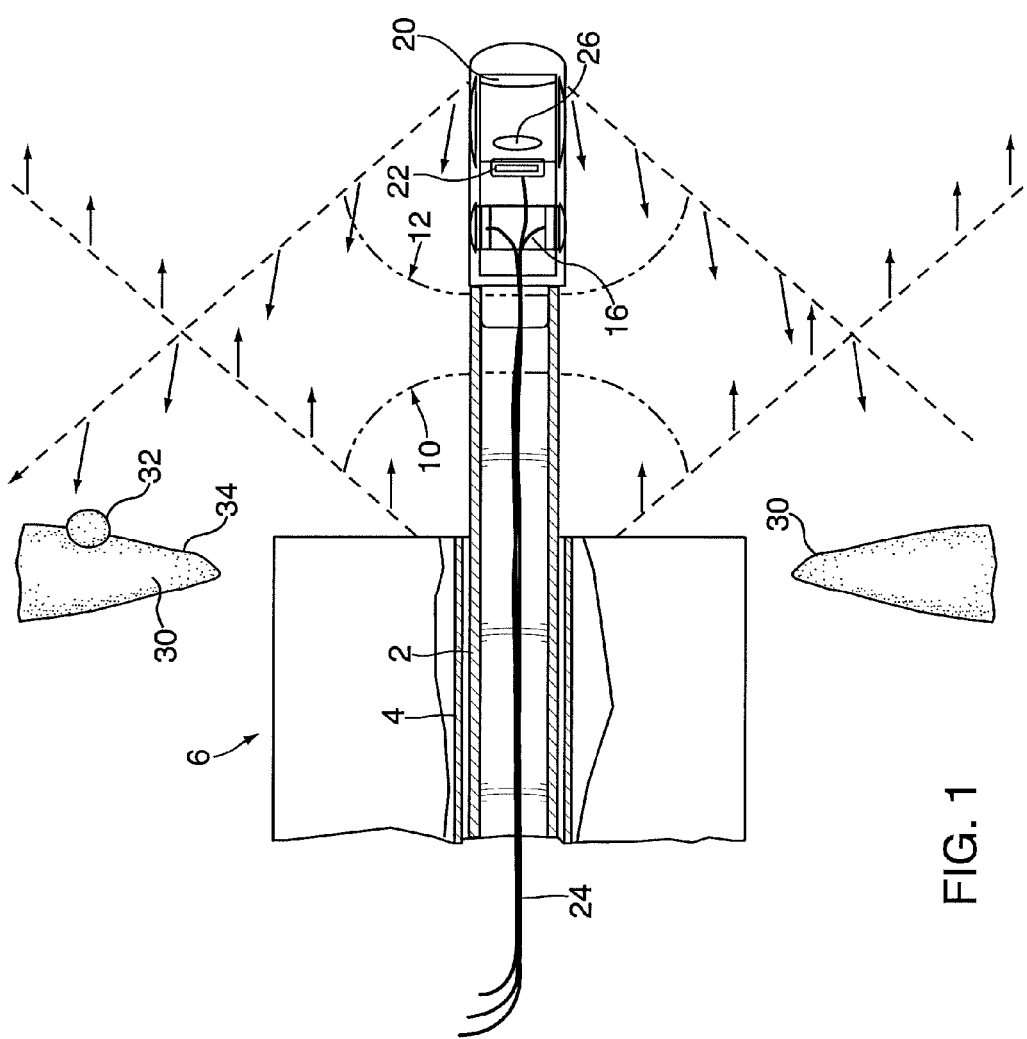
FIG. 1 is a schematic of one embodiment of an auxiliary endoscopic imaging catheter of the invention.

FIG. 1 is a schematic representation of the distal portion of an auxiliary endoscopic imaging catheter 2, according to one embodiment of the present invention. Auxiliary endoscopic imaging catheter 2 is shown exiting a working channel 4 of a primary endoscope 6. A forward-looking field of view 10 of primary endoscope 6 is augmented by a side and rearward-looking field of view 12 of auxiliary endoscopic imaging catheter 2. Both fields of view 10 and 12 are 360° around the longitudinal axis (not shown) of primary endoscope 6 and auxiliary endoscopic imaging catheter 2, respectively. Auxiliary endoscopic imaging catheter 2 includes illumination component 16, which illuminates 360° around catheter 2 and correlates with the field of view 12 of auxiliary endoscopic imaging catheter 2.

The side and rearward-looking field of view 12 of auxiliary endoscopic imaging catheter 2 is enabled by a distal mirror or lens 20, which reflects the side and rearward-looking image onto the imaging element or camera 22. Imaging element or camera 22 transmits electronic signals comprising the images through wire 24 to a camera control unit (not shown). The camera control unit converts the electronic signals to video images which may be displayed on a monitor (not shown). Optionally there may be one or more lens 26 between mirror 20 and camera 22.

In FIG. 1, a tissue fold 30 has a growth 32 (possibly a polyp), which is located on the distal side 34 of fold 30. Growth 32 is outside of, and cannot be seen or detected by, forward-looking field of view 10 of main endoscope 6. However, it is within, and thus can be seen and detected by, the side and rear looking field of view 12 of auxiliary endoscopic imaging catheter 2.

Figure 2:
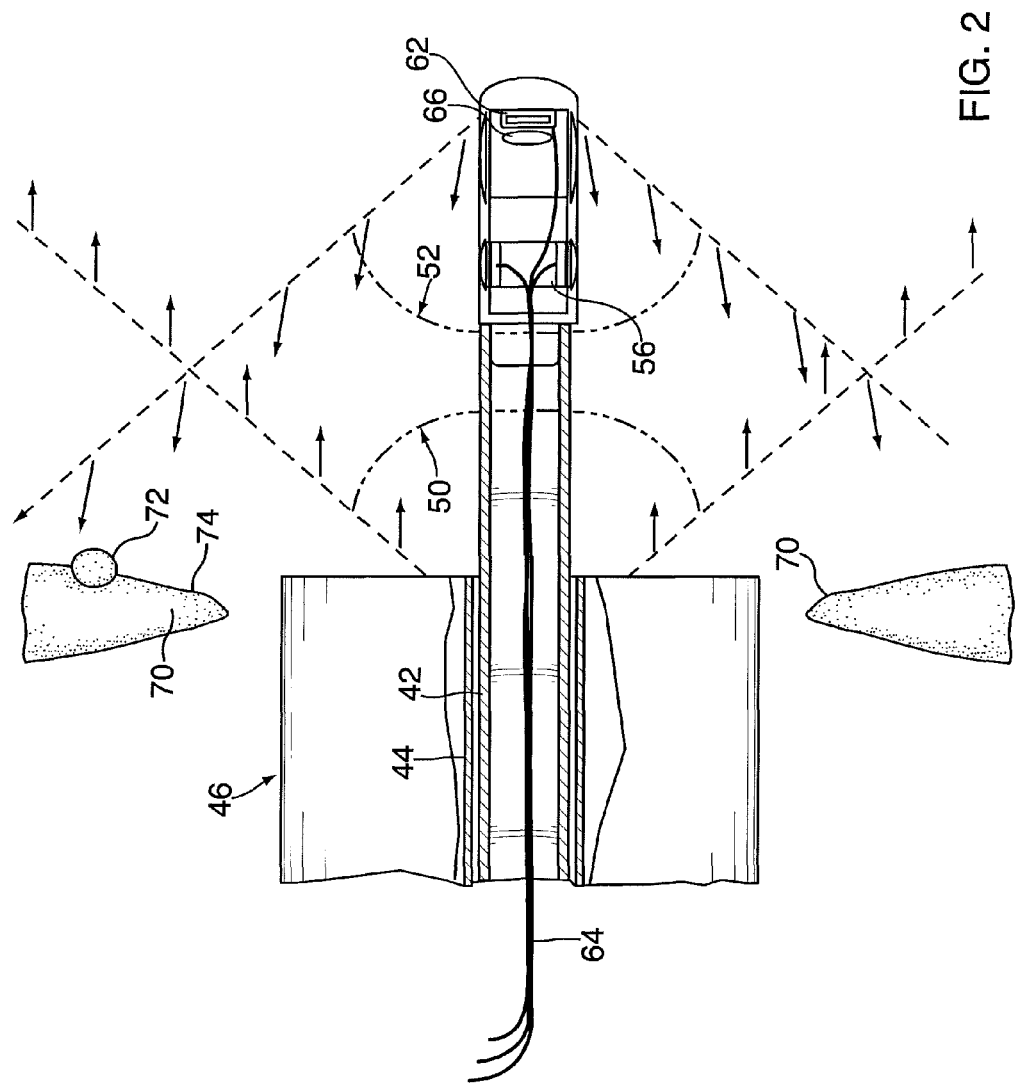
FIG. 2 is a schematic of another embodiment of an auxiliary endoscopic imaging catheter of the invention.

FIG. 2 is a schematic representation of the distal portion of an auxiliary endoscopic imaging catheter 42, according to another embodiment of the present invention. Auxiliary endoscopic imaging catheter 42 is shown exiting a working channel 44 of a primary endoscope 46. A forward-looking field of view 50 of primary endoscope 46 is augmented by a side and rearward-looking field of view 52 of auxiliary endoscopic imaging catheter 42. Both fields of view 50 and 52 are 360° around the longitudinal axis (not shown) of primary endoscope 46 and auxiliary endoscopic imaging catheter 42, respectively. Auxiliary endoscopic imaging catheter 42 includes illumination component 56, which illuminates 360° around catheter 42 and correlates with the field of view 52 of auxiliary endoscopic imaging catheter 42.

The side and rearward-looking field of view 52 of auxiliary endoscopic imaging catheter 42 is enabled by an imaging element or camera 62, which receives the side and rearward-looking image. Imaging element or camera 62 transmits electronic signals comprising the images through wire 64 to a camera control unit (not shown). The camera control unit converts the electronic signals to video images which may be displayed on a monitor (not shown). Optionally there may be one or more lens 66 positioned proximally to camera 62.

A tissue fold 70 has a growth 72 (possibly a polyp), which is located on the distal side 74 of fold 70. Growth 72 is outside of, and cannot be seen or detected by, forward-looking field of view 50 of main endoscope 46. However, it is within, and thus can be seen and detected by, the side and rear looking field of view 52 of auxiliary endoscopic imaging catheter 42.

Figure 3:
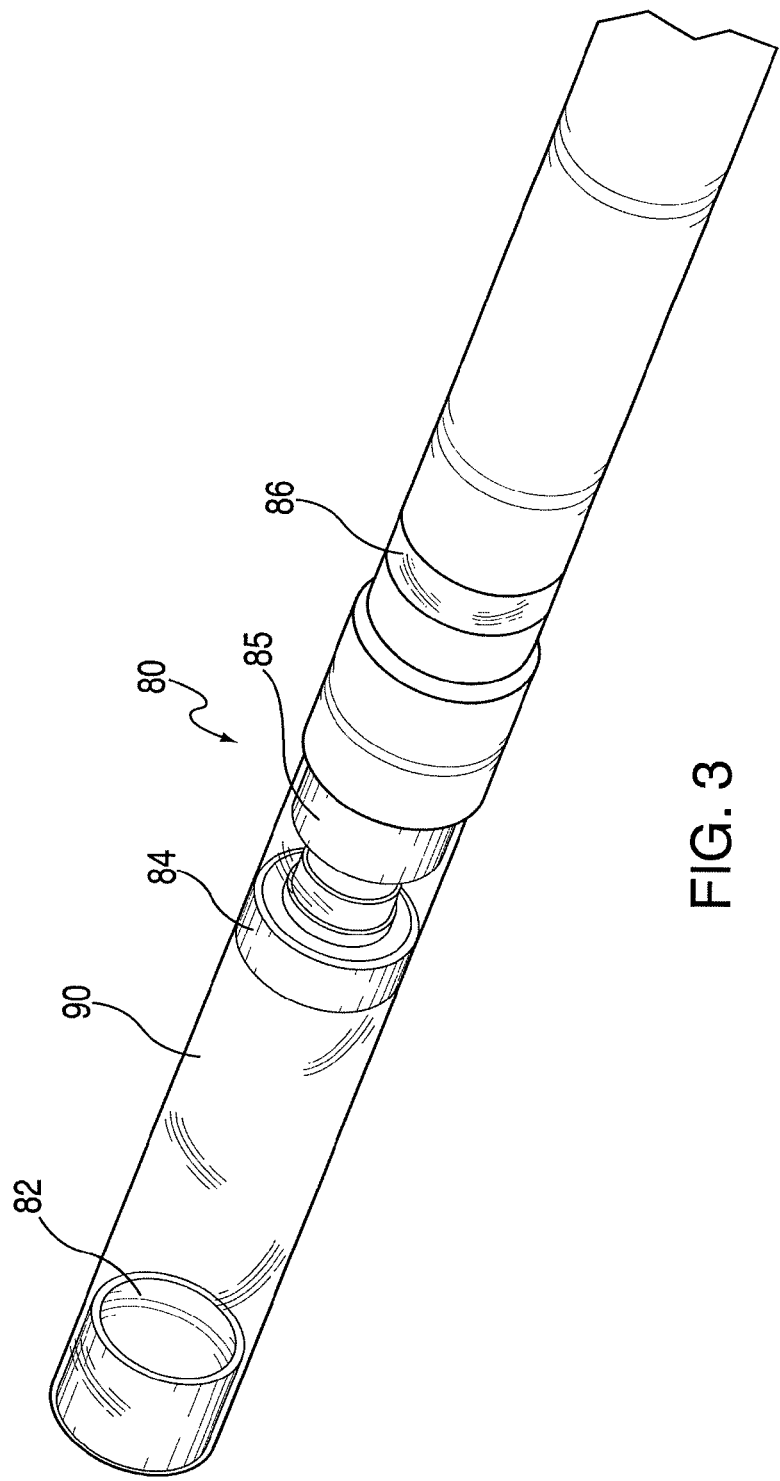
FIGS. 3 and 4 are each an oblique view of a distal section of an auxiliary endoscope imaging catheter according to the invention.
Figure 4:
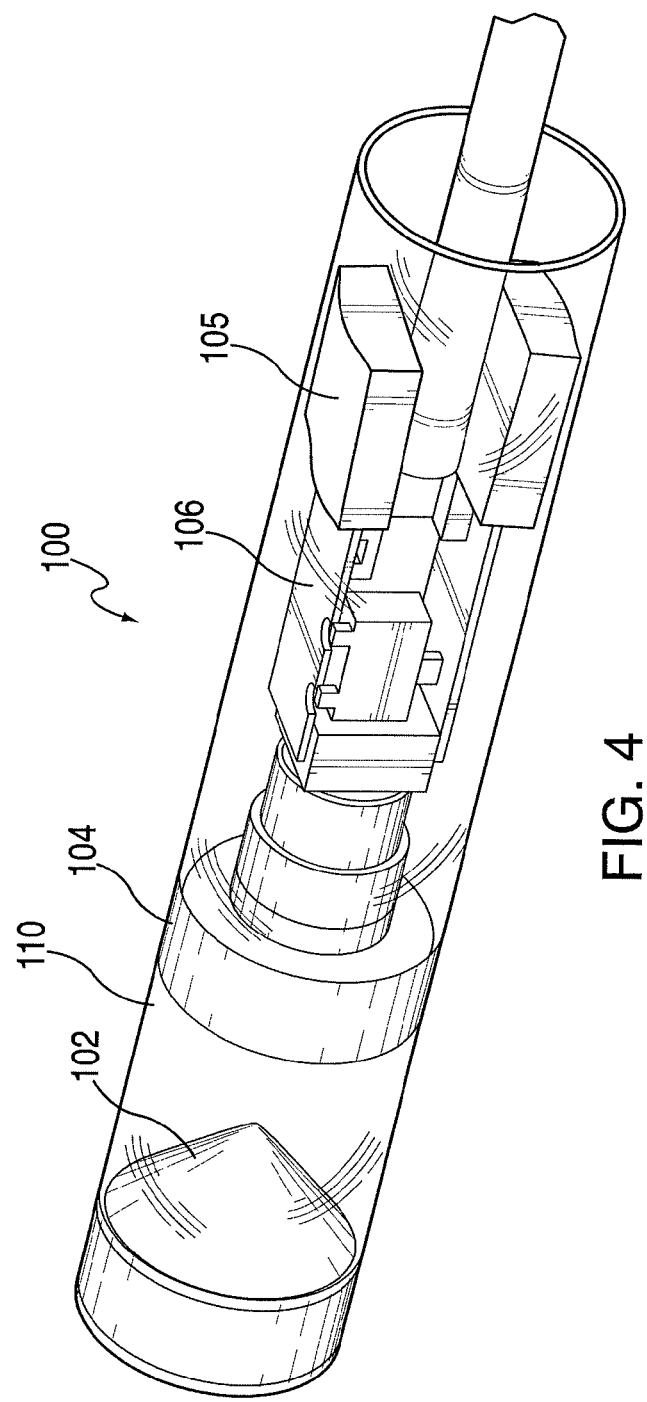

Schematic representations of distal ends of two different embodiments of the invention are shown in FIGS. 3 and 4. In FIG. 3, the distal section 80 of a catheter shaft has a proximally facing mirror or reflective surface 82 spaced apart from a lens or optics system 84 in communication with camera 85, with an illumination ring 86. The outer surface 90 of distal portion 80 is transparent in most or all of the space between mirror 82 and lens or optics system 84 or optionally extended and including camera 85 and/or illumination ring 86. Optionally the outer surface 90 between camera 84 and illumination ring 86 is opaque or translucent.

In FIG. 4, the distal section 100 of a catheter shaft has a proximally facing, reflecting mirror or reflective surface 102 spaced apart from a lens 104, with a camera 106 and a light source 108. The outer surface 110 of distal portion 100 is transparent in most or all of the space between mirror 102 and lens 104.

Before at least one embodiment of the invention is explained in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The description above relates to an endoscopic imaging catheter which is intended for use with a "standard" endoscope, such as endoscope 96. Such standard endoscope may be used in various medical imaging procedures in which an intrabody cavity or lumen is imaged, for example, anoscopy, arthroscopy, bronchoscopy, colonoscopy, cystoscopy, esophagogastro-duodenoscopy (EGD), trans-nasal esophagoscopy (TNE), laryngoscopy, laparoscopy, and sigmoidoscopy.

A standard endoscope includes an insertion tube whose distal section can optionally be articulated, for example, by an articulation knob (or other control), which may be part of an endoscope control/handle unit. Optionally, the control/handle unit is similar to an endoscopic control handle that is incorporated in a conventional endoscope used for intrabody procedures, such as biopsy. The insertion tube may be detachable from the control/handle unit or in permanent connection. The diameter, length and flexibility of the insertion tube may depend on the procedure for which the endoscope is used. The endoscope may have one or more working channels, for example, for instrumentation, air insufflation, water irrigation, suction and/or light, for example as commonly used in the art. For example, if the insertion tube is used for colonoscopy, the diameter of the working channel which is integral to the insertion tube thereof may be from about 3 mm to about 4 mm, optionally, from about 3.2 mm to about 4.2 mm. Optionally, the insertion tube may have varying flexibility over its length.

In one embodiment of the invention, an endoscopic imaging catheter 2 or 42 as described above is inserted via a biopsy/working channel 4 or 44, longitudinally traversing the insertion tube through the working channel. In other embodiments, an imaging catheter according to the invention can be integral to the standard endoscope. Optionally, an imaging catheter is sheathed before being inserted into a biopsy/working channel. Optionally or alternatively, a sheath covers the endoscope (or at least an insertion tube) and includes a channel and/or elongate extension for extension of the imaging catheter therethrough.

Optionally, a control handle is provided for manipulation of the imaging catheter, for example, for axial and/or rotational position control and/or for controlling of imaging and/or illumination features thereof. The control/handle unit optionally has a plurality of ports, for example, coupled to the biopsy/working channel, which are in communication with one or more channels in the insertion tube. Each port may allow the insertion of an endoscopic imaging catheter. For example, an endoscopic imaging catheter may be inserted via a biopsy tool port.

Optionally, the insertion tube has an imaging element mounted at a distal end thereof. Exemplary imaging elements include an image sensor, a tip of a fiber optic bundle, a charge coupled device (CCD) based sensor, a complementary metal oxide semiconductor (CMOS) based sensor and/or a radiation sensitive element. For clarity, this imaging element may be referred to herein as a frontal imaging element or as a main imaging element.

Optionally, an insertion tube has an illumination source mounted on the distal end thereof (or provided as a separate movable element, e.g., a catheter), for example, one or more light emitting diodes (LEDs) or fiberoptic light bundle(s). Optionally, an illumination source illuminates the field of view of the imaging element (and/or of imaging catheter). Optionally, a control unit is used for controlling and/or aiming frontal imaging element and/or illumination source. The cable or another port may be used for providing an illumination channel or fiber bundle that is connected to the frontal illumination source.

Optionally, the endoscopic imaging catheter may be extended out past the distal end of insertion tube, under visualization of the frontal/main imaging element. This may increase a safety of such extension.

According to some embodiments of the present invention, a reusable and/or a disposable sheath is placed over an endoscopic imaging catheter before insertion thereof into the intrabody lumen. A potential advantage of a disposable sheath is that it allows reusing the endoscopic imaging catheter multiple times. Optionally, a protective sheath is made of a layer of transparent flexible material, such as polyethylene terephthalate (PET), for example, 120-gauge PET, polyvinyl chloride (PVC), Polyethylene terephthalate copolymer (PETG), polyurethane, or other suitable transparent materials. Optionally, a sheath has a transparent segment that covers the distal end of an endoscopic imaging catheter. In such an embodiment, the rotatable shaft allows rotating an optical element without changing the orientation of the sheath. A potential advantage is that, the rotation of an optical element cannot damage the inner walls of an intrabody lumen, e.g., in an embodiment where the optical element is exposed. In some embodiments, with or without a sheath, a window is placed over the optical element. In some embodiments, the entire imaging catheter is rotated for achieving the above described lateral imaging.

It is expected that during the life of a patent maturing from this application many relevant systems and methods will be developed and the scope of the term illumination source, optical element, and imaging element is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A rearward viewing endoscopic imaging catheter, comprising:
   a longitudinally extending tubular member having a proximal end, a distal end, an outer surface, and a longitudinal axis;
   an optical element positioned within the tubular member distal end;
   an imaging sensor positioned within the tubular member distal end and in communication with the optical element,
   an illumination source that is located proximal to the imaging sensor and illuminates around the outer surface of the tubular member with a direction of illumination substantially perpendicular to the longitudinal axis,
   wherein the optical element and the imaging sensor are configured to capture an image comprising a rearward-looking conical field of view centered at the longitudinal axis of the tubular member of an organ or a corporeal wall encircling the intrabody lumen.

2. The rearward viewing endoscopic imaging catheter of claim 1, wherein the optical element comprises a reflecting element.

3. The rearward viewing endoscopic imaging catheter of claim 1, wherein the optical element is distal in relation to said imaging sensor.

4. The rearward viewing endoscopic imaging catheter of claim 1, wherein the illumination source is located proximally to the optical element.

5. The rearward viewing endoscopic imaging catheter of claim 4, where the illumination source illuminates side and rear fields of view of said imaging sensor, around the outer surface of the tubular member of the rearward viewing endoscopic imaging catheter.

6. The rearward viewing endoscopic imaging catheter of claim 4, where the illumination source illuminates the field of view of said imaging sensor, around the outer surface of the tubular member of the rearward viewing endoscopic imaging catheter.

7. The rearward viewing endoscopic imaging catheter of claim 1, wherein the illumination source comprises a single light source or a plurality of light sources.

8. The rearward viewing endoscopic imaging catheter of claim 7, wherein the illumination source comprises one or more LEDs.

9. The rearward viewing endoscopic imaging catheter of claim 1 which is capable of performing an endoscopic procedure.

10. A system comprising a rearward viewing endoscopic imaging catheter of claim 1 and a sheath sized and shaped to cover the endoscopic imaging catheter.

11. A method of probing a patient's organ or corporeal lumen, comprising:
    inserting a standard endoscope having a working channel with proximal and distal openings into the patient's organ or corporeal lumen;
    inserting a rearward viewing endoscopic imaging catheter of claim 1 into the proximal opening of the working channel; and
    advancing the distal tip of the rearward viewing endoscopic imaging catheter distally through the distal opening of the working channel,
    wherein forward and rearward images of the interior of the organ or a segment of an inner wall encircling the corporeal lumen can be viewed.

12. The method of claim 11, wherein said forward and rearward images are viewed substantially simultaneously.

13. A method of probing a patient's organ or intrabody lumen, comprising:
    inserting a rearward viewing endoscopic imaging catheter of claim 1 into the patient's organ or corporeal lumen; and
    advancing the distal tip of the rearward viewing imaging catheter further into the organ or corporeal lumen,
    wherein rearward images of the interior of the organ or a segment of an inner wall encircling the intrabody lumen can be viewed.

* * * * *